United States Patent [19]

Cockrem et al.

[11] Patent Number: 5,210,296
[45] Date of Patent: May 11, 1993

[54] RECOVERY OF LACTATE ESTERS AND LACTIC ACID FROM FERMENTATION BROTH

[75] Inventors: Michael C. M. Cockrem, Madison; Pride D. Johnson, Glenbeulah, both of Wis.

[73] Assignee: E. I. Du Pont de Nemours and Company, Wilmington, Del.

[21] Appl. No.: 718,542

[22] Filed: Jun. 20, 1991

Related U.S. Application Data

[63] Continuation of Ser. No. 615,510, Nov. 19, 1990, abandoned.

[51] Int. Cl.$^5$ .............................................. C07C 59/08
[52] U.S. Cl. .................................. 562/589; 562/580; 560/179
[58] Field of Search ................. 562/589, 580; 560/179

[56] References Cited

U.S. PATENT DOCUMENTS

| | | | |
|---|---|---|---|
| 2,331,948 | 10/1943 | Ward et al. | 562/589 |
| 2,350,370 | 6/1944 | Schopmeyer et al. | 562/589 |
| 2,420,234 | 5/1947 | Filachione | 562/589 |
| 4,467,034 | 8/1984 | Sukstach et al. | 435/139 |
| 4,698,303 | 10/1987 | Bailey | 562/589 |
| 4,749,652 | 6/1988 | Robison | 435/139 |
| 4,771,001 | 9/1988 | Bailey et al. | 435/139 |

FOREIGN PATENT DOCUMENTS

| | | |
|---|---|---|
| 0159585 | 4/1985 | European Pat. Off. |
| 0206373 | 3/1982 | Fed. Rep. of Germany |
| 907321 | 10/1962 | United Kingdom |

Primary Examiner—Paul J. Killos

[57] ABSTRACT

The production of high purity lactate ester or lactic acid from a concentrated fermentation broth by continuous acidification in the presence of an alcohol diluent with sequential or simultaneous esterification, distillation off of high purity ester, and, if desired, hydrolysis of the ester to high purity lactic acid.

9 Claims, 2 Drawing Sheets

RECOVERY OF LACTATE ESTERS AND LACTIC ACID FROM FERMENTATION BROTH

This application is a continuation, of application Ser. No. 07/615,510 filed Nov. 11, 1990, abandoned.

FIELD OF THE INVENTION

This invention relates to the production of high purity lactate ester or lactic acid from fermentation broth.

BACKGROUND OF THE INVENTION

Production of Lactic Acid by Fermentation

Lactic acid can be produced by the continuous or batch fermentation of sugars or other biomass streams such as hydrolized starch, sulfite waste liquor or cheese whey.

For a rapid and economic fermentation, the pH of the broth is usually maintained in the range of 5.2–6.8 by either (a) continuously removing lactic acid such as by extraction, or membranes, or ion exchange, or electrodialysis, or (b) continuously adding a base such as aqueous ammonia, calcium carbonate, calcium hydroxide, or sodium hydroxide, or (c) starting the fermentation with a growth medium with substantial buffering capacity, such as a calcium carbonate slurry.

In each case, the fermentation broth may or may not have the fermentation microorganisms or enzyme slurry removed.

Figure 1:
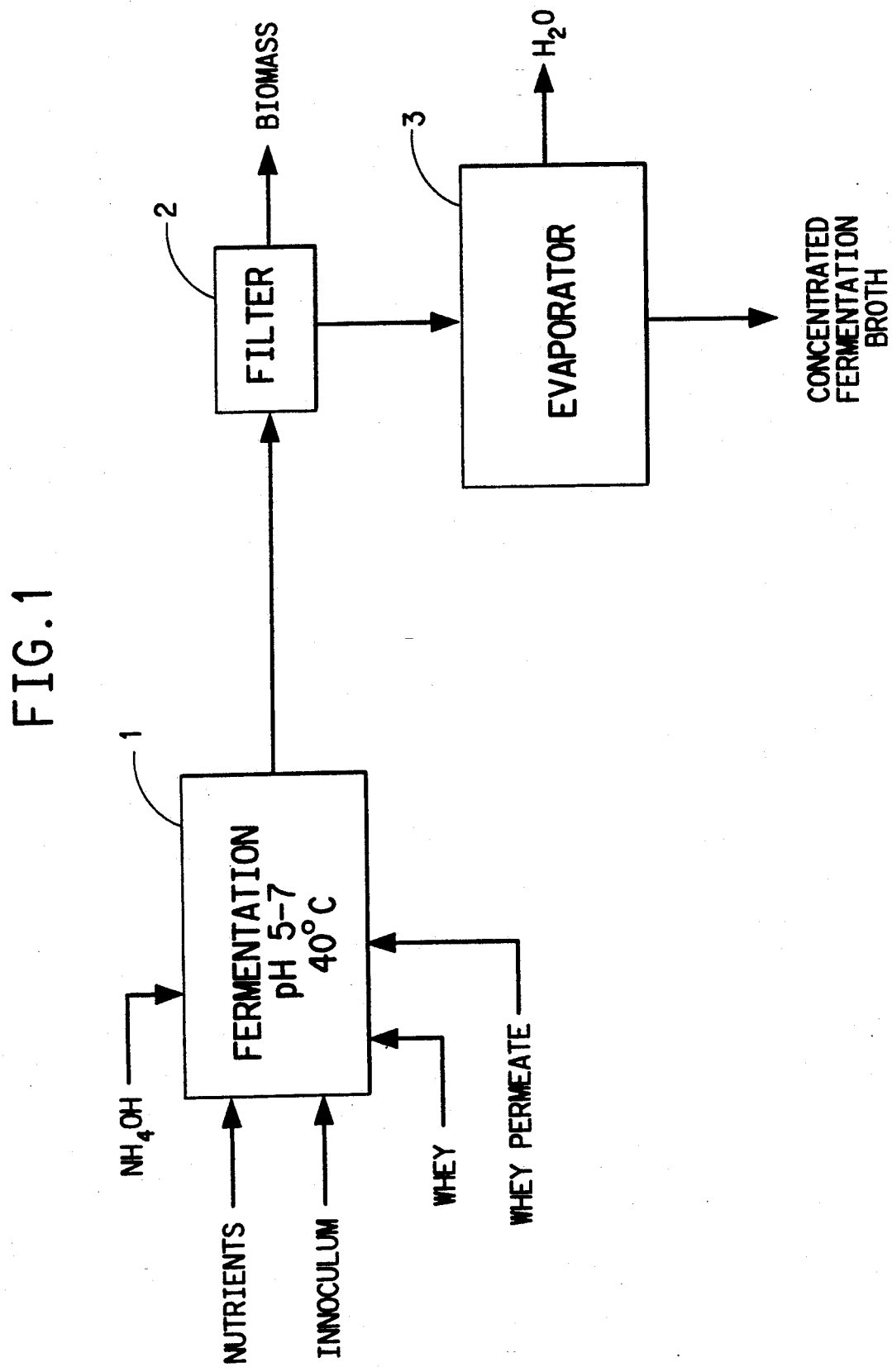

FIG. 1 illustrates one method of preparing a concentrated fermentation broth. Steps (1) to (3) are not part of the present invention, but are included for illustrative purposes only. Fermentation takes place in unit 1 where nutrients and whey/permeate are fermented at about 40° C., and a pH of about 5.6. The stream from the fermentation unit 1 containing about 10–12% lactate salt optionally is filtered by membrane filter or centrifuge 2, which removes the biomass and any other solids. The aqueous stream leaving the filter contains about 95 g/l of lactate salt and 2 g/l of succinate salt, 1 g/l of acetate salt and other impurities.

This stream from filter 2 goes to an evaporator 3, where excess water is removed to give a concentrated broth containing 10–40% water, the balance being primarily the lactate salt of the base used for fermentation pH control.

The Nature of Lactic Acid

Lactic acid of commerce is typically a nominal 88% lactic acid solution and 12% water. In reality, this is an equilibrium or non-equilibrium mixture of lactic acid monomers, dimers, trimers and other lactic polymers of low molecular weight, plus water.

Hereinafter, reference to "lactic acid" also includes mixtures of lactic acid with lactic acid dimers, trimers, low molecular weight polymers and water.

"Heat stable" lactic acid refers to acid which does not readily decolorize upon heating at 180° C. However, organic acid impurities such as acetic acid and some salt impurities such as calcium salts do not cause discoloration at 180° C. Thus, heat stable lactic acid need not be and is often not chemically pure. The term is a lower purity designation.

Lactic acid may exist as either of two stereochemical enantiomers or so-called "optical isomers"; D-(+)-lactic acid and L-(−)-lactic acid. A mixture of 99% "optical" purity is either (a) 99% D and 1% L, or (b) 1% D and 99% L.

A mixture of molecules of both forms is called a racemic mixture, or DL-lactic acid. The optical purity refers to the optical purity of the mixture of all forms of lactate, lactic acid, monomers, dimers, etc.

Salts of lactic acid also retain optical purity, as do compounds produced by chemical reaction of lactic acid, depending on the reaction and purification sequence.

The optical purity differs from the chemical purity. Hereinafter reference to purification of lactic acid means removal of non-lactic acid, non-water components. Some separation sequences will produce a chemically purified product which is racemic, while others will produce a chemically purified product which also has high optical purity.

Traditional Processes for Lactic Acid Purification

Direct distillation of lactic acid from a crude acidified fermentation broth at normal temperature and pressure for recovery of the lactic acid has not been acceptable because lactic acid forms high boiling internal esters as dimers and polymers during the distillation, resulting in poor yields of lactic acid (Smith and Claborn, JACS 61, 2727, 1939).

Repeated vacuum steam distillation has been used to produce monomeric lactic acid in high yield from a purified monomer-dimer-trimer mixture. However, this method requires a partially purified lactic acid to start with, entails expensive equipment, and is not effective in removing impurities (Leonard et al., IEC 40 57, 1948).

Fractional distillation at high vacuum and low temperature is too expensive for practical commercial operation.

Both the D and L forms of lactic acid can only be crystallized with great difficulty and in low yields. (Atkinson and Mavitnua, *Biotech Bioeno. Handbook*, Nature Press, 1983, pg. 1047).

These difficulties with simple processes lead to the traditional complex processes for producing lactic acid. For example, the fermentation pH is controlled by addition of calcium hydroxide or calcium carbonate. The resulting calcium lactate solution at pH 5–7 is then purified by a complex sequence of operations including one or several of each of the following steps in a variety of possible sequences involving both lactate salt streams and lactic acid streams; evaporation, acidification with sulfuric acid, filtration, washing of filtrate cake with cold water or with fresh broth, activated carbon bleaching, hydrogen sulfide metal precipitation, rotary vacuum filtration, and filter press filtration.

Specifically, Inskeep et al., IEC 44, pp. 1955–1966 (1952) report a process involving 7 filtration steps, one decanter, 7 stirred tanks, calcium lactate evaporators, and lactic acid evaporators. This process does not even produce a lactic acid product of high purity, rather it produces a crude 50% edible grade lactic acid and a 44% technical grade lactic acid.

The high solubility of calcium lactate in water makes losses in wash water and mother liquor a significant problem for purification of lactic acid via calcium lactate precipitation. Furthermore, to obtain high purity material this purification sequence must be followed by further purification steps.

Other Processes to Purity Lactic Acid

Other processes which have been tried to produce high purity lactic acid include multiple recrystallization of salts such as calcium lactate; solvent extraction using ether or a long chain amine; purification by ion exchange chromatography; electrodialysis; and separation and hydrolysis of lactic esters. If an alcohol is used as an extracting agent, extraction can be simultaneous or sequential to esterification.

Although the recrystallization technique can be successfully used to prepare a pure salt, say calcium lactate, this is expensive and the product must then be acidified such as with sulfuric acid to prepare the lactic acid.

Solvent extraction using ether requires very large volumes of ether. Any solvent which has high enough capacity for lactic acid to be economic, such as amyl alcohol or a tertiary amine, will also co-extract some water, salts and other organic acids. Thus, extraction alone does not economically product a product of high enough purity.

Recently electrodialysis has been proposed for purification of lactic acid (Colon, PhD thesis, 1986). Currently this process has two disadvantages: high cost and a product of intermediate purity.

The literature frequently mentions that high purity lactic acid can be prepared by forming an ester, purifying the ester by distillation or extraction, and then converting the ester back to lactic acid. (Atkinson and Mavituna, *Biotech Bioeno Handbook*, Nature Press (1983), p. 1047.) Many of the procedures reported in the literature concern the esterification of partially purified lactic acid to form a heat stable lactic acid product, and do not adequately address the needs for making a product of high chemical purity from a crude broth. Hereinafter, in the ester formation purification route the question of which alcohol is optimal for the complete process appears not to have been addressed prior.

In lactic acid purification it is known that lactic acid can be reacted with high excesses of methanol to produce methyl lactate, with methanol and water being drawn overhead to drive the reaction.

An alternate method using methanol as the esterifying alcohol involves removing the ester continuously from the pot to drive the reaction. The scheme involves bubbling excess hot alcohol, such as methanol vapor, through the lactic acid solution at a temperature above the alcohol boiling point, whereby the lactate ester produced is removed with the alcohol vapors and water (Filachione and Fisher, IEC 38, 228 (1946)). Approximately 9 moles of methanol are required to remove one mole of lactic acid from an 82% solution. Dramatically larger quantities of methanol are required for more dilute lactic acid feed solutions. This may be acceptable if a highly concentrated pure lactic acid feed solution is used. However, the disadvantage of this is that there is little liquid alcohol or liquid ester present in the reaction broth. This means that the broth becomes a thick residue of impurities and partially reacted material, limited the yield in a given cycle.

The composition of matter of 1-butyl lactate is and its preparation are disclosed in Gabriel et al. U.S. Pat. No. 1,668,806 (1928). They prepared 1-butyl lactate by dehydrating 70% lactic acid with excess 1-butanol at 117° C., followed by addition of HCl catalyst, followed by refluxing and esterification with addition excess 1-butanol and drawing a 1-butanol water azeotrope overhead. Nakanishi and Tsuda (Japanese Patent JP 46/30176 [71/30176]) consider production of 1-butyl lactate by extraction of an acidified crude fermentation broth with 1-butanol, followed by esterification of the extract phase. BASF (EP 159-285) considers production of isobutyl lactate by extraction of an acidified crude fermentation broth with isobutanol, followed by esterification of the extract phase, which was then distilled in vacuum 80° C./25 mbar to give a purified isobutyl lactate.

Kaplan (PhD Thesis, 1966) suggests that 1-butanol is preferable to methanol and ethanol for esterification. The use of methanol and ethanol in the esterification entails high alcohol to water ratios, and costly fractionating equipment for separating the alcohol, water and ester. The relative immiscibility of 1-butyl alcohol with water renders it preferably to the infinitely soluble ethyl and methyl alcohols for esterification when azeotropic distillation is used for completion of the reaction.

Kaplan proposes a process with a distillation column for continuous esterification of a nearly pure 50% food grade lactic acid. The overheads are condensed and the butanol phase is refluxed to the esterification column. There is no purge for light organics such as butyl-acetate, and thus his process will not make high purity product. The esterified column bottoms are fed directly to a second column where the butyl-lactate is separated from the high-boiling impurities. The purified butyl-lactate is steam hydrolized with an HCl catalyst. The HCl will cause dramatic corrosion problems in the lactic acid hydrolysis column, and will contaminate the product with chloride ions. Kaplan does not consider higher alcohols.

Smith and Claborn (IEC 32,262, 1940), note "It is more difficult to obtain a high yield of ester with methyl or isopropyl alcohol than it is with a long chain alcohol such as butyl, amyl, cetyl, lauryl and stearyl."

It is known that water removal can be carried out by using a higher alcohol that is sufficiently high boiling and slightly soluble in water (Filachione et al., JACS 70,526 (1948)). 1-Pentanol and higher alcohols have been esterified this way (Smith et al., IEC 32,692 (1940)). Grutein et al. (U.S. Pat. No. 1,160,595) also suggest that the higher molecular weight alcohols are preferable.

Azeotropic removal is necessary to remove the last traces of water economically from the esterification. Benzene has been used as an azeotropic entraining agent to remove water from a methanol-water-lactic acid reaction broth for the production of methyl lactate. The benzene-water overhead stream is condensed and the benzene and water phases separated. This process has the disadvantage of adding complexity due to the additional component.

SUMMARY OF THE INVENTION

This invention relates to a process for recovery of high purity lactate ester or lactic acid from fermentation broth containing ammonium lactate or other basic salt of lactic acid; acidifying in the presence of an alcohol of 4-5 carbon atoms as a diluent using continuous addition of sulfuric acid or other strong acid and crystallizing to precipitate out some or all of the basic salt of the strong acid; simultaneously or sequentially removing water from the acidified material as an alcohol water azeotrope overhead while also esterifying the lactic acid with the alcohol of 4-5 carbon atoms to form impure lactate ester; removing the crystals formed; distilling the lactate ester to remove impurities, residual water and excess butanol to yield high purity lactate ester; and hydrolyzing, if desired, the ester while removing alcohol and water to form high purity lactic acid.

Purities in excess of 99.5% lactic acid at concentrations approaching 90% lactic acid are obtainable, with retention of the optical purity of the feed material.

This invention is applicable to the purification of any crude fermentation broth containing an equilibrium mixture of salts of lactic acid and free acid itself, regardless of the exact sequence of steps used to perform the fermentation and prepare the crude broth. In particular, our invention relates to the use of ammonium as the dominant salt.

One aspect of the invention which distinguishes it from earlier work is that it produces a lactic acid or lactate ester product that is both of high optical purity and high chemical purity. It can also be used to produce lactic acid or lactate ester product that is optically racemic and of high chemical purity.

DETAILS OF THE INVENTION

This invention relates to the process for recovery of lactic ester or lactic acid from a crude fermentation broth containing primarily the salt of a strong or weak base with lactic acid, along with other components.

The process comprises the steps of:
(1) acidifying in the presence of an alcohol of 4-5 carbon atoms as a diluent while continuously adding sulfuric acid or other strong acid, and crystallizing to precipitate out some or all of the basic salt of the strong acid;
(2) simultaneously or sequentially with step (1) removing water from the acidified material as an alcohol water azeotrope while also esterifying the lactic acid with an alcohol of 4-5 carbon atoms to form impure lactate ester, which step may be undertaken in one vessel or several vessels in series;
(3) removing the crystals formed before or after neutralization of any excess acid, with or without cooling;
(4) distilling the lactate ester to remove impurities, residual water and excess alcohol to yield high purity lactate ester; and
(5) if desired, hydrolyzing the ester while removing alcohol and water to form high purity lactic acid.

It has been found that high yields of very high purity lactic ester or lactic acid can be produced economically by using a high boiling alcohol of 4-5 carbon atoms as the ester forming alcohol. This avoids the formation of dimer and polymer products and the hydrolysis or other reaction of the ester in the distillation step, thereby giving yields in the 85-98% range of 99+% purity lactate in lactic acid. By this technique optical purity of the lactic acid is retained as produced in fermentation. Virtually no racemization results.

cation of lactic acid by the

This purification of lactic acid by the high-boiling alcohol ester route to obtain high yields of high purity lactate ester or lactic acid and efficient alcohol recovery requires the following:
(1) efficient esterification with high yield and effective water removal;
(2) high yield distillation to separate out both light and heavy impurities with minimal loss of lactate ester;
(3) efficient hydrolysis to remove substantially all alcohol, with high conversion to lactic acid; and
(4) recovery of the alcohol by the formation of a heterogeneous alcohol/water azeotrope that can be separated to yield water-free alcohol.

The process of this invention is a low cost process for making very high purity product that has retained its optical purity. The steps that make this possible are:
(1) the ability to feed concentrated fermentation broth containing primarily a basic salt of lactic acid in aqueous solution, with or without removal of the biomass, directly to recovery;
(2) continuous acidification with strong acid in the presence of an alcohol diluent, which yields crystals of an appropriate size for simple removal by filtration and effective washing; and
(3) the use of a high-boiling alcohol esterification agent that is optimal for the steps of production of the ester, distillation of the ester, and, also, if necessary, hydrolysis of the ester.

A main feature of this invention is that a high purity lactate ester or lactic acid can be produced with the minimum number of process steps. Each process step can accommodate a wide variety of impurities, as is usually encountered in fermentation processes. No pretreatment is needed for the broth, and by this process the product is freed of all impurities including salts, organic acids, sugars, odors and cell residues. The process can be run either continuously or batchwise, and the optimum alcohols have been identified which maximize yield in the distillation and esterification steps with the minimum costs for esterification and distillation equipment.

Also, in the preferred form of the invention, with ammonium lactate as the main fermentation product and sulfuric acid as the acidify acid, the use of continuous stirring during acidification leads to the growth of large crystals which are far more easily removed and washed than the traditional calcium sulfate crystals.

The only waste from this process is the crystal precipitate which contains process impurities, still bottoms from the distillation step and water containing other fermentation impurities.

The preferred 1-butanol (n-butanol) ester is highly efficient in the hydrolysis step. Since it has a boiling point substantially lower than that of lactic acid, virtually all ester can be removed from residual lactic acid product, and n-butanol is readily removed from the reaction mass to drive the hydrolysis to substantially 100% completion. The n-butanol can readily be recovered and recycled in this process because it forms a heterogeneous azeotrope with water.

Thus, it has been determined that for optimum recovery if lactic acid from fermentation broth while retaining its optical purity, the use of n-butanol as the esterifying agent produces optimal results of high yield, high purity and optically unaltered lactic acid product. N-butanol has the ideal properties of (1) a boiling point at least 15° C. above the boiling point of water and at least 20° C. lower than the boiling point of lactic acid; (2) substantial immiscibility in water; and (3) the ability to form a heterogeneous azeotrope with water.

Another important facet of the present invention is the choice of base for neutralization of the lactic acid in the fermentation broth. This significantly affects the operation and economics of the subsequent lactic acid purification and recovery. Specifically in the preferred form of the present invention ammonium hydroxide is used to give a fermentation broth of pH 5 to 7. And, importantly, the ammonium sulfate salt produced can be crystallized into a readily filterable form.

Also in the preferred practice of the present invention, draft tube baffled crystallizers instead of stirred tanks are used to produce the lactic acid ester giving the desired easily filterable ammonium sulfate crystals.

The economy of this invention is related to the cost of recovery of dry alcohol for recycle to the esterification. This is related to the amount of water removed per unit of alcohol taken overhead and to the split of water between the heavy and light phases of the heterogeneous azeotrope. This can be seen in Table 1, which shows the "water efficiency", the weight of water passing into the heavy phase per weight of water in the alcohol phase. This shows that the condensed azeotrope of 1-butanol with water can be split into a heavy and light phase, where the heavy phase has 2.1 times the amount of water as the light phase. This number must be high for economical water removal because the light overheat phase contains 20% water that needs to be dried in a separate distillation column before reflux to the esterifier if high rates and good yield are to be obtained. The heavy phase contains 70,000 ppm alcohol which is stripped before that water can be reused in the fermentation or discarded. Of the butanols, 1-butanol is the most efficient for water removal. As the Table shows the higher the alcohol, the more efficient it is for water removal. However, physical properties such as the high viscosity of very high molecular weight alcohols limit their use.

TABLE 1

| | Alcohol Normal Boiling Point °C. | Overhead Vapor Azeotrope Molar Efficiency mol water mol alcohol | Condensed Heterogenous Phase Water Efficiency g water lower g water upper |
|---|---|---|---|
| Homogeneous Azeotropes | | | |
| ethanol | 78.5 | .1 | |
| iso-propanol (2-propanol) | 82.3 | .5 | |
| tert-butanol (2-me-2-propanol) | 82.8 | .6 | |
| propanol | 97.2 | 1.3 | |
| Heterogeneous Azeotropes | | | |
| iso-butanol (2-methyl-1-propanol) | 108.4 | 1.8 | 1.3 |
| (tert amyl) | 102.3 | 1.8 | |
| 2-butanol (sec) | 99.5 | 1.9 | |
| 2-methyl-1-butanol | 128.0 | 2.3 | |
| 3-methyl-2-butanol | 112.9 | 2.4 | |
| 3-pentanol | 115.6 | 2.6 | 3.4 |
| 2-pentanol | 119.3 | 2.8 | |
| 1-butanol | 117.7 | 3.3 | 2.1 |
| iso-pentanol (iso-amyl) | 132.0 | 6.0 | |
| pentanol (n-amyl) | 138.0 | 6.0 | |
| c-pentanol | 140.9 | 6.8 | |
| 2-ethyl-1-butanol | 148.9 | 6.8 | 20.1 |
| hexanol | 158.0 | 11.6 | 21.6 |
| 1-octanol | 195.0 | 65.0 | |
| 2-butyl octanol | 253.4 | 403.0 | 2939 |
| decanol | 283 | greater than 3000 | |

Also studied were the efficiency of ester distillation for purification and ester hydrolysis to determine if indeed these higher alcohols are optimal. In contrast to much earlier work, it was found that to prepare high purity esters it is necessary to carefully distill off "light" impurities with boiling points less than that of the ester, and then distill the ester away from "heavy" impurities with boiling points greater than that of the ester. Thus there are three reasons against using higher alcohols in the distillation step.

Firstly, lactate esters can decompose and transesterify and can also react at the free hydroxy group on the lactate part of the ester. For example, two molecules of octyl-lactate can react to form octyl-lactyl-lactate plus octyl alcohol. This reaction is driven by the elimination of the octyl alcohol overhead. The octyl-lactyl-lactate is then a yield loss in the distillation of octyl-lactate from light or heavy impurities. To minimize this reaction, temperatures lower than 150°-180° C. must be used, depending on contact time.

Furthermore, the racemization (loss of purity) is less at lower temperatures. To obtain distillation at these low temperatures, very low pressures must be used for higher alcohol esters, and the distillation column size becomes prohibitively expensive.

Secondly, some unreacted lactic acid remains in the esterification pot. This will distill at a boiling point close to that of butyl lactate, or less than that of higher esters. Thus, in trying to distill higher esters, lactic acid will distill. Unfortunately, lactic acid will also dehydrate under such conditions of temperature and pressure and a polymer will form. This will have high viscosity and will elevate the boiling point of the distillation bottoms further.

Therefore, lower boiling esters are favored in the distillation process.

In fact, it would seem obvious that methyl lactate would be the preferred ester for the distillation step since the temperature at which methyllactate boils at atmospheric pressure is only 143° C. However, it is not in fact the optimum, because as the methyl-lactate distillation is started first methanol distills overhead, then water, then methyl-lactate, then lactic acid. Thus, there is a hot solution of water and ester present in the distillation tower which brings about hydrolysis of the ester. The rate of hydrolysis in such operations can be significant (Colon et al., J. ACS., 76,6074 (1953)).

Consider Japanese Patent JP 62/26249 (87/26249) for the production of $C_1-C_6$ lactate esters by relfuxing crude lactic acid with alcohol in aqueous sulfuric acid (pH 2.3), followed by pH adjustment to 6.0 to 8.5 with aqueous sodium hydroxide, and distillation of the ester with benzene as an entraining agent. Here the benzene is required in the distillation of the methyl-lactate to ensure good yields in that distillation step. We have found that by selecting the optimal alcohol for esterification, we can eliminate the added complexity of using benzene in the ester distillation.

Yield in the distillation of the ester is affected by two factors, namely, hydrolysis of the ester back into acid due to residual water, and formation of dimer and polymer products by reactions between ester, unreacted acid and impurities. Distillation yield losses due to hydrolysis are lessened by using an alcohol with a boiling point greater than that of water.

TABLE 2

| | Normal Boiling Points | |
|---|---|---|
| Lactate Ester of | Alcohol °C. | Lactate Ester °C. |
| ethanol | 78.5 | 154 |
| iso-propanol (2-propanol) | 82.3 | 167 |
| 1-propanol | 97.2 | 169 |
| tert-butanol (2-methyl-2-propanol) | 82.8 | >175 |
| 2-butanol (sec-butanol) | 99.5 | >180 |
| iso-butanol (2-methyl-1-propanol) | 108.4 | 182 |
| 1-butanol | 117.7 | 187 |

TABLE 2-continued

| Lactate Ester of | Normal Boiling Points | |
|---|---|---|
| | Alcohol °C. | Lactate Ester °C. |
| 2-methyl-2-butanol (tert amyl) | 102.3 | >185 |
| (dl)-3-methyl-2-butanol | 112.9 | >190 |
| 3-pentanol (sec-amyl) | 116.1 | >195 |
| 2-pentanol | 118.9 | >195 |
| (l)-2-methyl-1-butanol (iso-amyl) | 129.0 | 198 |
| pentanol (n-amyl) | 138.0 | 206 |
| c-pentanol | 140.9 | >200 |
| 2-ethyl-1-butanol | 146.3 | |
| hexanol | 158.0 | 221 |
| 1-octanol | 195.0 | 256 |
| 2-butyl octanol | 253.4 | |
| decyl | | 283 |
| dodecyl | | 310 |
| tetradecyl | | 335 |

TABLE 3

Determination of the Optimum Alcohol for Ester Distillation

| Alcohol Type | Ethanol | Butanol | Hexanol | Octanol |
|---|---|---|---|---|
| Alcohol molecular weight | 46 | 74 | 102 | 130 |
| Alcohol NBP | 79 | 117 | 158 | 195 |
| Lactate Ester MW | 118 | 146 | 174 | 202 |
| Ester NBP | 154 | 187 | 221 | 256 |
| Pressure for 119° C. overhead | 251.19 | 74.99 | 21.88 | 3.80 |
| Density at 119° C. (lb/ft 3) | .0756 | .0279 | .0097 | .0020 |
| Vapor Flux for 1000 lb/hr LA in lb/hr of ester | 1711 | 2078 | 2456 | 2844 |
| D min for f - 0.50 feet = sqrt(4/pi. flux/sqrt dens. 1/f) (units of feet-sec-lb) | 2.19 | 1.97 | 4.20 | 6.75 |
| Relative Column Diameter | 1.00 | 1.41 | 2.00 | 3.21 |

These calculations assume that the overhead condenser temperature is fixed at 119° C., and that this allows the bottoms temperature to be kept low enough to minimize decomposition while still obtaining adequate yield of ester.

Thus, it can be seen that for the purification of lactate esters by distillation, alcohols with boiling points greater than that of water which form hetergeneous azeotropes with water and have the lowest lactate ester boiling points, at least less than 200° C. at 760 mm Hg, are the preferred alcohols.

These preferred alcohols contain 4 or 5 carbon atoms and so include: iso-butanol (2-methyl-1-propanol, 1-butanol, 2-methyl-2-butanol (tert amyl alcohol), (DL, L or D)-3-methyl-2-butanol, 3-pentanol (sec-amyl alcohol), 2-pentanol, and ((DL, L or D)-2-methyl-1-butanol (iso-amyl alcohol). Note that two optical isomers (D-form and L-form) exist for each of the alcohols 3-methyl-2-butanol and 2-methyl-1-butanol, and that a mixed form DL can also be used.

Of these alcohols, 2-pentanol has the greatest water efficiency and iso-butanol the least. However, 1-butanol and iso-butanol are more readily available commercially in good purity. Iso-butanol has a lower water efficiency than 1-butanol, and is less economical. Thus, 1-butanol is the preferred alcohol for lactate ester purification by esterification in the process of the present invention.

Other hexanols can be used but require much larger distillation columns due to the need for lower pressure to maintain the lower temperature required for avoiding lactate decomposition. Higher alcohols are even less favorable.

Thus, it has been found that the optimum alcohols for purification of lactate ester by distillation are those containing 4 or 5 carbon atoms, which are optimum for the following reasons: for retention of optical purity, for minimization of equipment size, for minimization of energy requirements, and for maximization of distillation yield with minimization of side reactions.

As aforementioned, in the present process high purity lactic acid is produced by hydrolysis with water of the high purity lactate ester to produce lactic acid plus the alcohol, and then stripping the alcohol and any unreacted ester from the lactic acid-water product. To obtain low residual levels of the ester, high conversion of the ester driven by removal of the alcohol is needed, followed by economical removal of any residual ester such as by steam stripping. Here the more volatile the alcohol and ester are, the easier it is to remove them from the reaction broth. However, the lower molecular weight lactate esters form azeotropes with water which are rich in the ester, which makes them more difficult to hydrolyze. There is thus an optimum ester for the hydrolysis step alone, one that does not form an ester-water azeotrope which is rich in the ester, yet one that the alcohol formed is easily stripped. Pentyl and butyl lactates are favored, propyl-lactates, ethyl-lactate and methyl-lactate also being suitable.

Thus, the optimum esters as intermediates for lactic acid production will require a balance between needs for ester formation, ester purification and ester hydrolysis.

Additionally, the present invention encompasses an economical procedure to operate the esterification reactor or reactors which substantially reduces the number of equipment pieces, the process complexity and increases the yield of ester.

The calcium salts formed in the acidification of calcium lactate broth with sulfuric acid are often fine crystals that are difficult to filter (Inskeep et al., previously cited). There is no mention in the literature of the design of correct crystallization equipment nor the relationship of effective crystal washing to good yield, nor the selection of the appropriate filter for this task. As well as selecting the optimal alcohols, this invention pertains to the selection of correct equipment for these steps.

It has been found that the acidification of the basic salt of ammonium lactate must be undertaken in a continuous or semicontinuous manner to grow crystals which are the correct size for easy filtration and high efficiency washing.

Any suitably stirred vessel can be fed simultaneously with a concentrated fermentation broth containing a basic salt of lactic acid plus other impurities, a strong acid and an alcohol. The location of the feeds should preferably be below the liquid surface. Crystals of the basic salt of the strong acid are formed, and the lactic acid and alcohol react to form the lactate ester. The stirred reactor is heated to the boiling point and the alcohol-water azeotrope continuously removed overhead driving the reaction to the ester and also precipitating more crystals as the water is removed. The liquid product is continuously drawn from the reactor, and may pass directly to a suitable filter to remove the solids, or to further reactors or cooling and neutralization prior to filtration. The key to this equipment simplification is that the acidification and esterification can be completed simultaneously in a single reactor, or sequentially in a series of continuous reactors, in the presence of many of the crude materials present in the original fermentation broth. The crystal growth is aided in all cases by the presence of the alcohol as a diluent.

Furthermore, in the preferred form of this invention, it has been found that a fermentation broth predominantly composed of the ammonium salt of lactic acid when neutralized with sulfuric acid in the correct manner leads to crystals which are easily filtered and washed.

Figure 2:
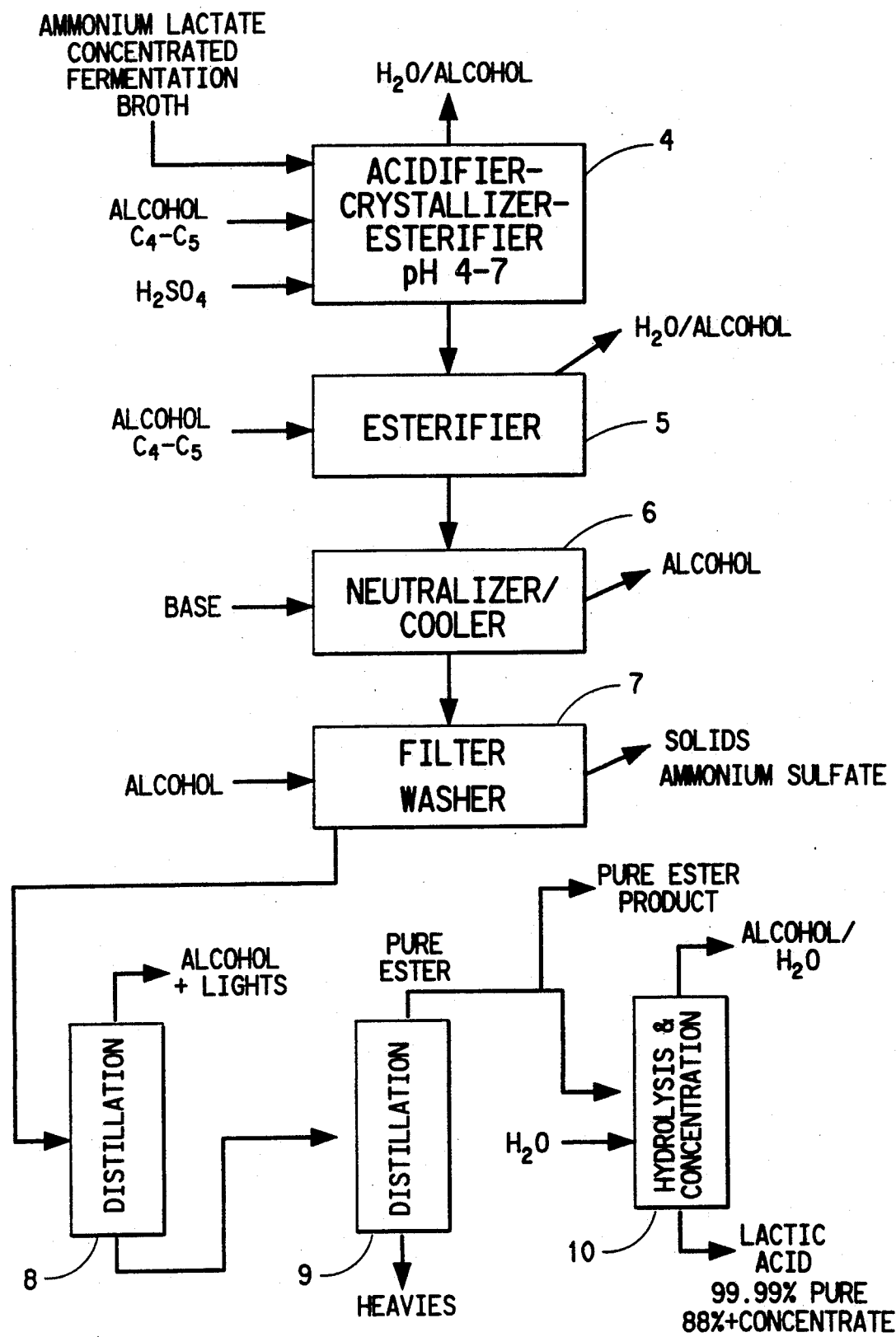

FIG. 2 schematically shows the preferred practice of the present invention.

The crude fermentation broth containing primarily the salt of a strong or weak base with lactic acid, but also other components, for example, as from Unit 3 in FIG. 1, but also possibly from any other source, goes to the simultaneous acidification and crystallization Unit 4 where alcohol is added as a diluent and a strong acid such as sulfuric acid is added to a pH of about 1.5 to form lactic acid and the base salt of the strong acid, for example, ammonium sulfate. Esterification will occur in this vessel, and an alcohol water azeotrope may be taken overhead. The partially or fully esterified product from Unit 4 may optionally pass to Unit 5, which may be one or several reactors in series for further simultaneous esterification and crystal growth and water removal overhead as the water alcohol azeotrope.

The product from Unit 4 or Unit 5 then passes to Units 6 and 7. These Units may be in the illustrated order, or in reverse order with Unit 7 preceding Unit 6. The reaction broth is neutralized, cooled and the crystals removed by filtration. The crystals are washed with dry alcohol to increase yield. The wash alcohol may be recycled or passed to Unit 8 with the mother liquor.

In Unit 8 the alcohol and other light impurities are separated from the ester and heavy impurities, which pass to Unit 9 where the ester is distilled overhead under vacuum to separate it from the heavy impurities.

The pure ester product then may be optionally hydrolyzed with water to lactic acid in Unit 10 in the presence of an acid catalyst, which may be lactic acid under pressure or a catalyst bed containing strong acid ion exchange resin. Butanol is removed and the product stream is concentrated by the removal of water, yielding the final product stream consisting of 88% aqueous lactic acid of 99+% purity having the optical purity of the original fermentation lactic acid.

EXAMPLE 1

Six gallons of concentrated fermentation broth containing 59% ammonium lactate, 13% other salts and fermentation residues, and 28% water is charged to a 50-gallon glass lined reactor with a recurve three-blade agitator. Ten gallons of 1-butanol are added. The stirrer is started at 130 rpm such that the impellor tip speed is not excessive for crystal growth. Next 1.5 gallons of 98% sa is metered into the reactor continuously over the next 30 minutes. Crystals which are predominantly composed of ammonium sulfate but include some of the fermentation salts and other components grow in this time. The reactor is sampled and more sulfuric acid added until the pH is between 1.0 and 1.5.

The heat to the reactor is started and a 1-butanol-water azeotrope withdrawn overhead through a short column to a condenser. The condensed overhead phase separates into a light butanol rich and a heavy water rich phase. Reflux of the light phase is taken from a reverse dean and stark trap back to the column. Fresh dry 1-butanol is added to the pot to replace butanol which is removed overhead. The pot temperature is raised slowly to 115° C. As the water content of the pot drops, the overhead phase ceases to be two phases, and only a portion of the light butanol rich phase is returned to the column. As the water content of the pot drops, the crystals grow in size. In all, an additional 10 gallons of 1-butanol is added during the course of the reaction.

Upon completion of the reaction, the pot is cooled by drawing a vacuum of between 50 and 300 mm Hg on the condenser and receiver. Some reflux is maintained on the column. Considerable butanol is drawn off overhead. The residual material is a suspension of crystals in a solution which is primarily butyl-lactate ester and 1-butanol, but contains some soluble organic and inorganic impurities, plus residual sulfuric acid and lactic acid. This mixture is then carefully neutralized to pH 6.66 to 8.0 by the addition of anhydrous ammonia or other anhydrous base. Mixing is maintained. Slight additional crystal growth occurs.

The suspension is now filtered by draining the entire reactor pot contents into a 2.5 foot diameter Buchner funnel with a woven gauze filter cloth. A vacuum is applied to the funnel and clarified liquor drawn into a receiver. The salts are easily washed using dry 1-butanol, which may be saved for use in the next batch of esterification or added to the filtrate for distillation. Dry 1-butanol is particularly useful because it does not appreciably dissolve salt impurities.

The filtrate now contains butanol, butyl-lactate, light ester impurities such as butyl-acetate, heavy ester impurities such as butyl-succinate, and other residual impurities. The filtrate is now distilled using any convenient available distillation sequence to produce a high purity butyl-lactate. The temperature of the final heavy pot bottoms should not exceed 150°-160° C. to minimize yield loss. This requires that the distillation be conducted at pressures as low as 50 mm Hg.

EXAMPLE 2

Concentrated fermentation broth at pH 5.5 containing ammonium lactate and other acids and salts and impurities and 25% water at a flowrate of 6000 pounds per hour is continuously fed to a 10,000 gallon draft-tube baffled stirred crystallizer with a steam heated jacket maintained at a constant temperature of 104° C. Simultaneously charged to the reactor is 12,000 pounds per hour of 1-butanol which may be recycled from other steps of the process after a suitable drying procedure. Simultaneously charged to the reactor is 2000 pounds per hour of concentrated sulfuric acid, controlled to maintain a pH in the reactor in the range of 1.0 to 1.6. All the addition points are located subsurface in a region of intense mixing, but with mixing velocities of less than 1500 ft/min. Simultaneously vapors containing butanol and water are drawn off overhead at a rate of 4000 pounds per hour and a liquid product is drawn off to maintain a constant level in the reactor. This reaction product is largely butyl-lactate and butanol, with suspended solid crystals which are predominantly ammonium sulfate. These crystals are of large size suitable for easy removal and effective washing in a filter or screening centrifuge.

EXAMPLE 3

The reaction product of Example 2 is fed to a second continuous draft tube baffled reactor in series with additional 1-butanol feed of 6000 pounds per hour and further takeoff of butanol and water overhead.

EXAMPLE 4

The product of either Example 2 or Example 3 is fed to a continuous stirred draft tube baffled flash vessel where butanol is drawn overhead continuously under vacuum at 100-300 mm Hg and dry ammonia gas fed subsurface to neutralize excess catalyst.

What is claimed is:

1. A process for recovering high purity lactate ester from a concentrated fermentation broth comprising the steps of:
   (1) simultaneously mixing a strong acid, an alcohol, and a concentrated fermentation broth which contains mainly basic salts of lactic acid, which react to form a crystal precipitate comprising basic salts of the strong acid and an impure lactate ester of the alcohol;
   (2) removing water from the mixture as a water/alcohol azeotrope which can be accomplished either sequentially or substantially simultaneously with step (1);
   (3) removing the crystal precipitate from the mixture; and
   (4) distilling the impure lactate ester to remove impurities, and recovering the high purity ester.

2. The process of claim 1 wherein the alcohol contains from 4 to 5 carbon atoms.

3. The process of claim 2 wherein the alcohol contains an alcohol selected from the group consisting of: iso-butanol (2-methyl-1-propanol), 1-butanol, 2-methyl-2-butanol (tert amyl alcohol), (DL, L or D)-3-methyl-2-butanol, 3-pentanol (sec-amyl alcohol), 2-pentanol, and (DL, L or D)-2-methyl-1-butanol (iso-amyl alcohol).

4. The processes of claims 1 to 3 comprising the additional step of hydrolyzing the lactate ester to form high purity lactic acid.

5. The processes of claims 1 to 4 wherein the concentrated fermentation broth contains at least 10% water and at least 45% ammonium lactate, and the strong acid is sulfuric acid.

6. The process of claim 5 wherein ammonium sulfate is crystallized out in draft tube baffled crystallizers.

7. The processes of claims 1 to 6 wherein the precipitated crystals are washed with dry alcohol.

8. The process of claim 1 wherein the fermentation broth contains ammonium lactate of at least 98% optical purity and the lactate ester is at least 97% optically pure.

9. The process of claim 4 wherein the lactic acid is at least 97% optically pure.

* * * * *